(12) United States Patent
Schirr et al.

(10) Patent No.: US 8,101,897 B2
(45) Date of Patent: Jan. 24, 2012

(54) LABORATORY APPARATUS FOR SIMULTANEOUSLY CARRYING OUT REACTIONS IN A PLURALITY OF SAMPLES

(75) Inventors: Andreas Schirr, Hamburg (DE); Gerd Eckert, Hamburg (DE); Markus Lapczyna, Hamburg (DE)

(73) Assignee: Eppendorf AG, Hamburg (DE)

( * ) Notice: Subject to any disclaimer, the term of this patent is extended or adjusted under 35 U.S.C. 154(b) by 0 days.

(21) Appl. No.: 12/088,182

(22) PCT Filed: Sep. 1, 2006

(86) PCT No.: PCT/EP2006/008560
§ 371 (c)(1),
(2), (4) Date: Jul. 18, 2008

(87) PCT Pub. No.: WO2007/036281
PCT Pub. Date: Apr. 5, 2007

(65) Prior Publication Data
US 2009/0032743 A1 Feb. 5, 2009

(30) Foreign Application Priority Data
Sep. 28, 2005 (DE) .......... 10 2005 046 583

(51) Int. Cl.
*G01J 1/32* (2006.01)
*G06M 7/00* (2006.01)
(52) U.S. Cl. .................. 250/205; 250/221
(58) Field of Classification Search .......... 250/205, 250/553, 559.04, 559.05, 559.07, 559.08, 250/221; 315/151; 362/800
See application file for complete search history.

(56) References Cited

U.S. PATENT DOCUMENTS

| 5,169,601 A * | 12/1992 | Ohta et al. ............ 422/73 |
| 6,207,946 B1 | 3/2001 | Jusoh et al. |
| 6,225,912 B1 * | 5/2001 | Tanaka et al. ............ 340/641 |
| 6,825,930 B2 * | 11/2004 | Cronin et al. ............ 356/328 |
| 2003/0127609 A1 | 7/2003 | El-Hage et al. |

FOREIGN PATENT DOCUMENTS

| DE | 197 49 333 A1 | 3/1999 |
| EP | 1 079 667 A2 | 2/2001 |
| EP | 1 149 280 B1 | 10/2001 |
| JP | 2000111476 | 4/2000 |
| JP | 2003-514223 | 4/2003 |
| JP | 2003-344267 | 12/2003 |
| WO | 01/35079 | 5/2001 |
| WO | 03/002991 A2 | 1/2003 |
| WO | 03/017728 A1 | 2/2003 |
| WO | 200/1057924 A1 | 7/2004 |
| WO | 2005/079121 A2 | 8/2005 |

\* cited by examiner

*Primary Examiner* — Georgia Y Epps
*Assistant Examiner* — Pascal M Bui Pho
(74) *Attorney, Agent, or Firm* — Rankin, Hill & Clark LLP

(57) ABSTRACT

The invention relates to a laboratory apparatus for simultaneously carrying out reactions in a plurality of samples which are arranged in an array. The apparatus includes an illumination device, which emits illumination light onto the samples, a detection device, which generates a signal dependent on the light intensity of the light coming from the samples and which forwards the signal to an evaluation device, and a monitoring device for checking the functioning of the illumination device. The illumination device has a plurality of light-emitting diodes assigned in each case to one of the samples, and the monitoring device has electrical devices which can be used to perform an electrical functional check of the light-emitting diodes. The monitoring device is adapted to generate a signal when a functional disturbance of a light-emitting diode is ascertained.

18 Claims, 1 Drawing Sheet

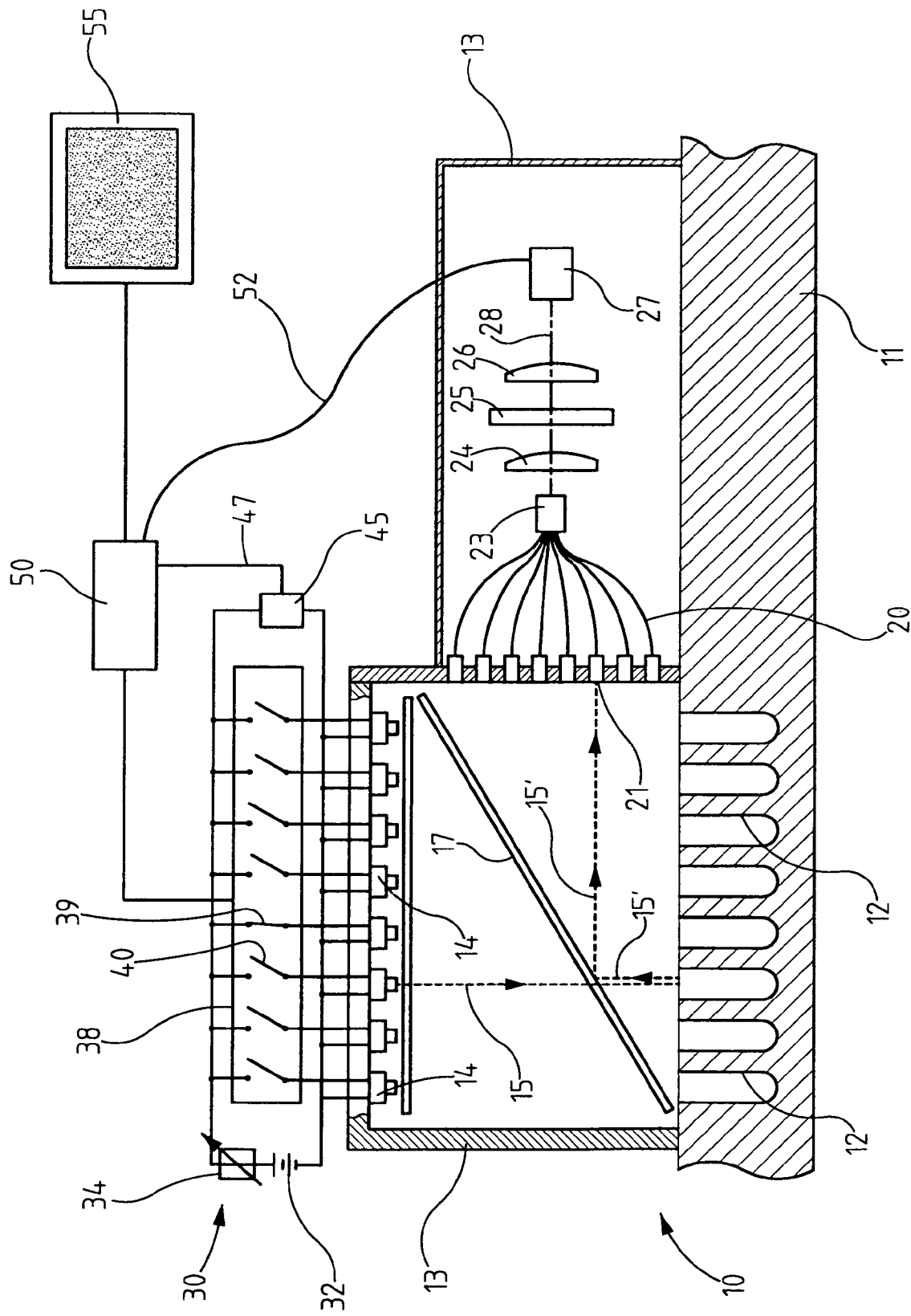

LABORATORY APPARATUS FOR SIMULTANEOUSLY CARRYING OUT REACTIONS IN A PLURALITY OF SAMPLES

BACKGROUND OF THE INVENTION

The invention relates to a laboratory apparatus for simultaneously carrying out reactions in a plurality of samples, which are arranged in an array.

A laboratory apparatus of this type can be, e.g., an apparatus for carrying out nucleic acid amplification procedures (hereinafter called PCR reactions), in which the quantitative formation of the amplification products (PCR products) during the PCR reactions is measured by optical means. This specific form of PCR is called real-time PCR reaction. The description hereinafter will focus mainly on PCR apparatuses of this type for illustration purposes without a limitation being intended.

It is common in real-time PCR reactions to measure mixed samples, which, for optical measuring purposes, contain fluorescence indicators that emit fluorescence signals after excitation by light of a suitable wavelength, whereby the intensity of the fluorescence signal depends on the quantity of PCR product formed. Usually, the increase of PCR products with progressing reaction time can be followed in real-time PCR reactions by means of an increase in the intensity of the fluorescence signals measured. However, measurements using transmission are also possible.

The technique of real-time PCR is described comprehensively in Neusser, Transkript Laborwelt no. 2/2000; "Echtzeit-PCR-Verfahren zur Quantifizierung von PCR-Produkten". Reference shall thus be made to the content of this citation such that further explanations on possible fluorescence indicators and other aspects of this procedure are not required.

The plurality of samples that are processed simultaneously in laboratory apparatuses of this type, for example simultaneously undergo PCR amplification cycles, usually are arranged in an array. A thermocycler tempers the samples, e.g., to the various PCR temperature stages, e.g. using a temperature gradient in one or more of these stages. For observation and/or measurement of the quantitative development of PCR products formed, the laboratory apparatus of this type comprises an illumination device that emits light of suitable wavelength onto the samples. This light source can, e.g., be a blue or white light-emitting diode; other alternatives are, e.g., halogen lamps, xenon lamps, laser diodes, lasers, etc. Moreover, there may be provided additional optical components, e.g. in order to filter the illumination light or focus it onto the samples.

For measurement of the light signals, usually a fluorescence generated by the PCR products, a detector is provided that generates measured values in a manner dependent on a measured light intensity. It is also feasible to provide more than one detector. The detector can, e.g., be a CCD chip or a photo-multiplier or can contain a CCD chip or a photo-multiplier. The intensity of the light usually increases with the number of PCR products. However, procedures are known, in which the increase of PCR products is observed by means of a decrease of the fluorescence.

Furthermore, the apparatus usually also includes optical devices that define a beam path leading from the illumination device to the reaction samples and from there to the detector. These optical devices comprise, e.g., a dichroic mirror that is arranged between the illumination device and the samples and that allows the excitation light originating from the illumination device to pass to the samples and that reflects a fluorescence signal with a longer wavelength that is emitted from the optically-excited reaction region to the detector that is disposed, e.g., on the side. Usually, a number of other optical components are provided, for example filters, lenses, etc., which are upstream of the detector.

However, a fluorescence or a change of fluorescence will not be observable in all samples. If, e.g., the starting product to be amplified by means of PCR is not present in the sample at all, no fluorescence will be observed. However, in samples of this type it is not feasible to distinguish whether or not the lack of fluorescence truly originates from a lack of the starting product or if the excitation light source might possibly be defective, meaning that excitation of fluorescence never occurred. Both lead to the same result. In this context, it would be very important to be able to determine unambiguously why no fluorescence is observed, since real-time PCR measurements are used, e.g., in medical diagnostic work-ups. False diagnoses can have disastrous consequences.

An apparatus of this type is known from US 2003/0127609 A1 and includes a monitoring device that can monitor the functioning of the illumination device. This monitoring device consists of an additional light detector that is arranged such that illumination light is applied to it by the illumination light source. If this additional light detector determines that no illumination light impinges on it, the user is alerted to the fact that the illumination light source is defective.

It is considered to be a disadvantage of this solution that an additional costly detector is needed which, in addition, requires quite some space. The optical monitoring also appears to be failure-prone, e.g. because the absence of interfering light from any source other than the illumination device and interference-free impingement of the illumination light on the detector is required for correct monitoring. It is also considered to be disadvantageous that US 2003/0127609 A1 operates with a single illumination light source such that failure of the light source would render the entire device unusable. For selective illumination of a single sample of the plurality of samples, a mechanically complex relative motion between illumination device and samples is provided at this time. In the examples shown, a microtiter plate is moved mechanically, whereby the samples are contained in the receptacles of the microtiter plate.

The prior art also knows laboratory apparatuses that operate using more than one light source. WO 03/002991 A2, e.g., provides an arrangement of light-emitting diodes as illumination device. In this context, one light-emitting diode each is assigned to each of the samples. There is no monitoring of the light-emitting diodes for correct functioning such that in this case no unambiguous statement with regard to the cause can be made if there is no fluorescence.

BRIEF SUMMARY OF THE INVENTION

It is the object of the invention to provide a laboratory apparatus that can simply and reliably monitor the functioning of the illumination device.

The object is met by a laboratory apparatus comprising:
an illumination device, which emits illumination light onto the samples,
a detection device, which generates a signal dependent on the light intensity of light coming from the samples, wherein the detection device forwards the signal to an evaluation device, and
a monitoring device for checking the functioning of the illumination device,
wherein the illumination device has a plurality of light-emitting diodes, each of which is assigned to one of the plurality of samples, and the monitoring device has electrical devices which can be used to perform an electrical functional check of the light-emitting diodes, and wherein the monitoring device is adapted to generate a signal when a functional disturbance of one of the plurality of light-emitting diodes is ascertained.

According to a preferred embodiment of the invention, the illumination device consists of a plurality of light-emitting diodes, which each are assigned to one of the plurality of samples, whereby advantageously, only one of the light-emitting diodes is triggered to emit illumination light at any given time. The monitoring device does not include optical, but electrical devices that can be used to carry out an electrical functional check of the light-emitting diodes, whereby the monitoring device is furthermore embodied for generating a signal when a functional disturbance of a light-emitting diode is ascertained. The term, light-emitting diodes, shall also encompass laser diodes.

The advantages of the invention are that electrical functional monitoring can be carried out using simple means, whereby a multitude of alternative options is available for implementation thereof. For example, it would be feasible to measure on each of the light-emitting diodes whether or not, e.g., an electric current flows through the diode or, e.g., how the voltage behaves across the diode. Moreover, the electrical properties of the device supplying electric current to the light-emitting diode could be monitored.

Moreover, the laboratory apparatus can advantageously include a thermocycler that can be triggered by a control device for tempering of the plurality of samples to certain reaction temperatures. Advantageously, the thermocycler can be triggered for generating a temperature gradient. Moreover, the laboratory apparatus according to the invention can advantageously be embodied for carrying out real-time PCR reactions.

It is feasible to provide a dedicated source of electrical power for each of the light-emitting diodes. However, it is advantageous for all light-emitting diodes to be supplied by the same source of electrical power. In particular, it is advantageous for the electrical power source to be designed as a constant-current source and for the monitoring device to measure the output voltage of said constant-current source that is provided as described. The constant-current source is advantageous in that the diode current no longer depends on the input voltage and the voltage drop on the diode. Circuits for embodiment of the constant-current source are sufficiently well-known according to the prior art.

In order to take into account shifts of electrical parameters, e.g. due to aging or drift effects of the light-emitting diodes, the monitoring device can further advantageously include comparative devices for comparing the output voltage measured to a predetermined output voltage range.

In a simple embodiment, the signal of the monitoring device can display that a disturbance of the illumination device has been determined without identifying the defective light-emitting diode in any more detail. Based on such limited information all measuring results would potentially be associated with errors and therefore basically need to be discarded. However, considering that usable results are available for all samples to be assigned to all light-emitting diodes that work without disturbance, discarding all results would be a waste of the samples used, which are usually expensive, and of the time used. Therefore, the monitoring device is advantageously embodied for generating a signal that identifies the light-emitting diode whose function is disturbed. This information is directly available, e.g., if the function is monitored locally on each of the light-emitting diodes. However, using decentralized monitoring of function, e.g. by monitoring the direct current source, this information can also be obtained easily, e.g. by evaluating the information specifying which light-emitting diode was triggered for illumination at which time and at which time the functional disturbance was determined, or, e.g., by means of the switch triggering the light-emitting diodes at the time the disturbance is recognized. This evaluation can proceed, e.g., in an evaluation and control device that contains both the control intelligence for controlling the laboratory apparatus and the evaluation intelligence for receiving, recording, and evaluating the measuring signals from the detector. Upon identification of the light-emitting diode with disturbed function, it is advantageous to use all measurements in which no disturbance occurred, while the measurement during which the illumination diode showed a disturbance of function can be discarded selectively.

Moreover, in a use of the laboratory apparatus at a later time, the sample site to which the defective light-emitting diode is assigned can be specifically disregarded, while all other sample sites can be used. The laboratory apparatus can include a display on which the non-usable position is displayed for the user, e.g. by displaying the light-emitting diode showing a disturbance or by displaying the corresponding sample site in the array. Accordingly, it is feasible to keep using the laboratory apparatus with this restriction in mind, there is no need to wait, e.g., for the damaged light-emitting diode to be replaced, e.g., by a service technician.

A light-emitting diode that is determined to be defective can be taken into account, e.g., in the new calibration of the device or in the calibration of the device for a new dye. For example, the measuring result to be assigned to said light-emitting diode can be omitted in the formation of a mean.

BRIEF DESCRIPTION OF THE DRAWING

The invention is illustrated in more detail with reference to the accompanying drawing FIGURE, which shows a real-time PCR apparatus as an exemplary embodiment of a laboratory apparatus according to the invention.

DETAILED DESCRIPTION OF THE INVENTION

With reference to the accompanying drawing FIGURE, the apparatus 10 includes a common thermocycler 11, which is shown schematically and which comprises receptacles 12 for receiving a plurality of samples. In operation, reaction vessels, in which one PCR sample each comprising a fluorescence indicator is contained and which are not shown here, are placed in the receptacles 12.

A lid housing 13 comprising an illumination device comprising a plurality of light-emitting diodes 14 is placed on the thermocycler 11. One light-emitting diode 14 each is assigned to one receptacle 12. Preferably, the light-emitting diodes 14 are arranged in the form of an array, like the receptacles 12. During the measurement, the light-emitting diodes 14 are preferably switched on and off individually by the control and evaluation device 50 such that only one assigned receptacle 12 is irradiated at any given time.

An exemplary beam path from one light-emitting diode 14 to a detector 27 is shown by 15, 15'. The light 15 is emitted by the light-emitting diode 14 and can then pass through a short pass filter (not shown) that is used to filter out long-wavelength fractions. Moreover, the light 15 can be focused onto the assigned receptacle 12 by an array of lenses that also is not shown here. In the process, the excitation light 15 passes through a beam splitter 17 that preferably is completely translucent in this direction.

Preferably, a dichroic mirror that allows excitation light 15 to pass at high efficiency, but reflects the emitted fluorescence signal 15' of a longer wavelength at high efficiency, is used as beam splitter 17.

The light 15 emitted by the light-emitting diode 14 is meant to excite a fluorescence indicator that is present in a PCR sample in the receptacle 12. It needs to be of a suitable wavelength for this purpose, in order to be able to excite fluorescence. After excitation, the fluorescence indicator emits a fluorescence signal 15'. The beam splitter 17 is structured such that the fluorescence signal 15' impinging on it is reflected towards the side. The optical arrangement shown therefore corresponds to a typical 90° measuring set-up for fluorescence measurements.

The reflected fluorescence signal 15' then proceeds onto a detector 27 detecting the fluorescence intensity. Various optical devices that can be used to image the fluorescence signal 15' on the detector 27 are placed upstream of the detector 27. In more detail, the optical devices comprise a plurality of light conductor fibers 20 comprising light entry surfaces 21 that each are assigned to one receptacle 12 and/or to the fluorescence signals 15' that are emitted from the receptacles 12 and reflected at the beam splitter 17. The light entry surfaces 21, in turn, are preferably arranged in the form of an array, like the light-emitting diodes 14 and the receptacles 12.

The light conductor fibers 20 are combined into a bundle 23 at their exit end. Providing for bundling has the effect that the fluorescence signals from all receptacles 12 exit from the exit ends of the respective fibers relatively close to each other, namely in the proximity of the optical axis 28 of the detector 27. Having the exit surface be narrowly limited is preferable in order to collimate the exiting fluorescence light beams whose directions of propagation differ only to a small extent from one light conductor fiber to another light conductor fiber. This is of advantage, in particular, if the filters downstream of the exit end are interference filters whose spectral transmission characteristics depend on the angle of incidence onto the filters.

The fluorescence signal 15' is then displayed onto the detector 27 by the light conductor bundle 23 via further optical devices, e.g. a lens 24, a band-pass filter 25, and a further lens 26. The filters can also be automatically changeable in order to adapt the apparatus to various fluorescence indicators.

The light-emitting diodes 14 are all connected in parallel to a direct current source 30, which essentially consists of a supply voltage source 32, e.g. a power supply unit that is current-stabilized by means of a common electronic circuit 34, e.g. a reverse-coupled transistor. Other supply voltage sources and other electronic circuits for current stabilization are also feasible.

The flow of current to each of the light-emitting diodes 14 is governed by an assigned switch 39, 40 that can assume a closed and an open position. The plurality of switches 39, 40, which are combined into a switch unit 38, are closed or opened by the control and evaluation device 50 by means of control signals. In the example shown, switch 39 is closed and switch 40 is open.

Arranging the light-emitting diodes 14 in an array allows the targeted triggering of each individual light-emitting diode 14 to be implemented in preferred fashion by means of switches that govern all light-emitting diodes of one column and/or all light-emitting diodes of one row. By closing one column switch and one row switch, current is applied to the light-emitting diode that is situated both in the selected column and in the selected row.

A monitoring device 45 monitors the output voltage of the constant-current source 30 supplying electric current to the light-emitting diodes 14. It can be observed that the output voltage drops if current flows through a functioning light-emitting diode. This voltage drop is essentially equal for all light-emitting diodes if equal light-emitting diodes are used. Taking into account aging and drift effects, e.g., a voltage range can be defined, in which the output voltage measured should be, if current is applied to a functioning light-emitting diode. The monitoring device 45 is connected to the control and evaluation device 50 in a communicating fashion. In the exemplary embodiment shown, the monitoring device 45 receives control signals when one of the light-emitting diodes 14 is being switched on. It then measures the output voltage and compares the voltage measured to a voltage range that has been laid down as being permissible. If this permissible range is exceeded or not reached, an error message is issued via the signal line 47 to the control and evaluation device 50, which determines from the time at which the error signal occurred or, e.g., from the positions of the switches 39, 40, which light-emitting diode 14 caused an erroneous output voltage and therefore must be classified as having a disturbed function. In the evaluation of the luminescence intensity values received by the detector 27 via signal line 52, the results originating from the sample, which is to be assigned to the light-emitting diode 14 whose function is disturbed, are not taken into account and/or are displayed as erroneous. Moreover, the light-emitting diode 14 whose function is disturbed can be displayed on a display device 55 together with a notice indicating that the corresponding receptacle to be assigned should no longer be used. This error message is no longer issued as soon as the light-emitting diode 14, whose function is disturbed, is replaced. The error message can display, e.g., graphically, the sample site in the array that is assigned to the erroneous light-emitting diode 14 and therefore is not usable. Moreover, a corresponding notice can be displayed such as that it can be read by the user.

The invention claimed is:

1. A laboratory apparatus for simultaneously carrying out reactions in a plurality of samples which are arranged in an array, comprising:
    an illumination device having a plurality of light-emitting diodes, each of which is assigned to and emits illumination light onto one of the plurality of samples,
    a detection device, which generates signals dependent on the intensity of light coming from the samples,
    a monitoring device for checking the function of the illumination device, wherein the monitoring device includes electrical devices that perform an electrical, non-optical, functional check of the light-emitting diodes, and wherein the monitoring device generates a signal when a functional disturbance of one of the plurality of light-emitting diodes is ascertained, and
    an evaluation device that receives signals from the detection device and the monitoring device, wherein the evaluation device selectively discards a signal from the detection device for an assigned light-emitting diode whose function has been ascertained as being disturbed.

2. The laboratory apparatus according to claim 1, wherein only one of the light-emitting diodes is triggered at any given time to emit illumination light.

3. The laboratory apparatus according to claim 1, wherein the same current source is used to supply a constant current to each of the plurality of light-emitting diodes.

4. The laboratory apparatus according to claim 3, wherein the monitoring device measures an output voltage of the current source.

5. The laboratory apparatus according to claim 4, wherein the monitoring device includes comparative devices for comparing the measured output voltage to a predetermined output voltage range.

6. The laboratory apparatus according to claim 1, wherein the signal generated by the monitoring device identifies the light-emitting diode whose function is disturbed.

7. The laboratory apparatus according to claim 1, wherein the apparatus includes a thermocycler that can be triggered by a control device for tempering of the plurality of samples to certain reaction temperatures.

8. The laboratory apparatus according to claim 7, wherein the apparatus is adapted to carry out real-time polymerase chain reactions.

9. The laboratory apparatus according to claim 7, wherein the thermocycler can be triggered to generate a temperature gradient.

10. The laboratory apparatus according to claim 6, wherein a display device is provided on which the disturbed light-emitting diode or an assigned sample site can be displayed.

11. The laboratory apparatus according to claim 2, wherein the same current source is used to supply a constant current to each of the plurality of light-emitting diodes.

12. The laboratory apparatus according to claim 11, wherein the monitoring device measures an output voltage of the current source.

13. The laboratory apparatus according to claim 12, wherein the monitoring device includes comparative devices for comparing the measured output voltage to a predetermined output voltage range.

14. The laboratory apparatus according to claim 8, wherein the thermocycler can be triggered to generate a temperature gradient.

15. The laboratory apparatus according to claim 7, wherein a display device is provided on which the disturbed light-emitting diode or an assigned sample site can be displayed.

16. The laboratory apparatus according to claim 8, wherein a display device is provided on which the disturbed light-emitting diode or an assigned sample site can be displayed.

17. The laboratory apparatus according to claim 9, wherein a display device is provided on which the disturbed light-emitting diode or an assigned sample site can be displayed.

18. A laboratory apparatus for simultaneously carrying out reactions in a plurality of samples which are arranged in an array, comprising:
   an illumination device having a plurality of light-emitting diodes supplied with current by a current source, each of which is assigned to and emits illumination light onto one of the plurality of samples;
   a detection device, which generates signals dependent on the intensity of light coming from the samples;
   a monitoring device for checking the function of the illumination device, wherein the monitoring device includes electrical devices that measure electrical properties of the light-emitting diodes or electrical properties of the current source supplying current to the light-emitting diodes, and wherein the monitoring device generates a signal when a functional disturbance of one of the plurality of light-emitting diodes is ascertained; and
   an evaluation device that receives signals from the detection device and the monitoring device, wherein the evaluation device selectively discards a signal from the detection device for an assigned light-emitting diode whose function has been ascertained as being disturbed.

* * * * *